(12) United States Patent
Lokhov

(10) Patent No.: US 9,844,586 B2
(45) Date of Patent: Dec. 19, 2017

(54) METHOD FOR PRODUCING AN ANTITUMORAL VACCINE BASED ON SURFACE ENDOTHELIAL CELL ANTIGENS

(76) Inventor: Petr Genrievich Lokhov, Moscow (RU)

( * ) Notice: Subject to any disclaimer, the term of this patent is extended or adjusted under 35 U.S.C. 154(b) by 0 days.

(21) Appl. No.: 12/545,518

(22) Filed: Aug. 21, 2009

(65) Prior Publication Data
US 2010/0316658 A1    Dec. 16, 2010

Related U.S. Application Data

(63) Continuation of application No. PCT/RU2007/000570, filed on Oct. 16, 2007.

(51) Int. Cl.
*A61K 39/00* (2006.01)
*A61P 35/00* (2006.01)
*C12N 5/071* (2010.01)
*C12N 5/09* (2010.01)

(52) U.S. Cl.
CPC .... *A61K 39/0011* (2013.01); *A61K 2039/515* (2013.01)

(58) Field of Classification Search
None
See application file for complete search history.

(56) References Cited

U.S. PATENT DOCUMENTS

| | | | | |
|---|---|---|---|---|
| 5,474,899 A | * | 12/1995 | Lisi | G01N 33/6869 435/7.1 |
| 5,656,441 A | * | 8/1997 | Faller | G01N 33/5005 435/29 |
| 5,811,522 A | * | 9/1998 | Wallace et al. | 530/387.3 |
| 6,004,554 A | * | 12/1999 | Thorpe | A61K 47/48561 424/136.1 |
| 2004/0022813 A1 | * | 2/2004 | Bystryn | 424/277.1 |
| 2004/0115174 A1 | * | 6/2004 | Gilboa et al. | 424/93.7 |

FOREIGN PATENT DOCUMENTS

| | | | |
|---|---|---|---|
| WO | WO2004/001004 | * | 12/2003 |
| WO | WO2006011060 | * | 2/2006 |

OTHER PUBLICATIONS

Barillari et al, Blood, 1999, vol. 94, pp. 663-672.*
Folkman, Nature Medicine, 1995, vol. 1, pp. 27-31.*

* cited by examiner

*Primary Examiner* — Karen Canella
(74) *Attorney, Agent, or Firm* — Nadya Reingand; Yan Hankin

(57) ABSTRACT

Accordingly to the method of the preparing of the tumor vaccine with the use of endothelial cells, live endothelial cells are treated with a protease at mild (non-deadly for cells) conditions, the splitted surface antigens are collected, the treatment of live endothelial cells is repeated after intervals which are necessary for the recovery of the surface antigens by the cells, surface antigens are accumulated until their necessary quantity is reached, the quality of the vaccine is controlled thereafter. The technical result obtained with the use of this invention consists in the enhancement of the efficiency of oncological disease treatment due to the damage of the tumor vessels caused by overcoming of the immune tolerance of organism to the endothelial cells (EC) of tumor vessels. Here one means the overcoming of immune tolerance namely to activated EC, which allows to damage mainly to the tumor vessels by the immune system.

18 Claims, 2 Drawing Sheets

METHOD FOR PRODUCING AN ANTITUMORAL VACCINE BASED ON SURFACE ENDOTHELIAL CELL ANTIGENS

This application is a Continuation of International Application No. PCT/RU2007/000570, filed Oct. 16, 2007, which claims priority to Eurasian Patent Application No. 200700940, filed Apr. 27, 2007, both of which are incorporated herein by reference in their entirety.

FIELD OF THE INVENTION

The invention pertains to the medical technologies namely to the immunotherapy of oncological patients and it could be employed in medicine for the therapy of oncological diseases and the prophylaxis of their relapses.

BACKGROUND OF THE INVENTION

The restricted possibilities of surgical methods and of the chemotherapy make urgent the further development of new methods of treatment of the oncological patients. Nowadays particular attention is given to the anti-angiogenic therapy which mode of action is based on the repression of the growth of tumor vessels.

The tumor development has two main stages: the prevascular and vascular ones. During the first stage the tumor grows receiving nutritive substances and oxygen by means of the their diffusion from the patient's vessels which does not allow the tumor to grow over the volume of few cubic millimeters. The following tumor growth requires it's transition to the second stage which is characterized by the tumor vascularisation (Folkman J., "What is evidence that tumors are angiogenesis dependent?" J. Natl. Cancer Inst., 1990, v.82, 4-6). The appearance of blood vessels strongly enhances the nutrition of the tumor which leads to it's intensified growth and augments the probability of metastases (Hanahan D., Folkman J. "Patterns and emerging mechanisms of the angiogenic switch during tumorigenesis". Cell, 1996, v. 86, 353-364). The use of anti-angiogenic substances results in the prevention of tumor vessels growth and accordingly in the suppression of the second phase of growth.

One of the well known ways of the tumor growth prevention is the vaccination of the patient aiming to overcome the immune tolerance in respect to endothelial cells (EC) lining the vessels' intima. The cell- and humoral cytotoxicity results in the death of EC which hinders the formation of tumor vessels and as consequence causes the destruction of the malignant cells. Various methods of the preparation of antigens for such vaccines are known; most close to our invention are vaccines based on the proper EC antigens.

Literature sources suggest the method of obtaining the vaccine based on the use of xenogeneic EC i.e. using endothelial cells from another biological species (e.g. Wei Y., "Immunotherapy of tumors with xenogeneic endothelial cells as a vaccine", Nature Medicine, 2000, v. 6, 1160-1166). The shortcoming of those vaccines is the presence of xenogeneic and in reality of ballast antigens that leads to the splitting of immune response between the latter and the antigens determining the specific response against EC.

From another source the vaccine based on allogenic antigens is known, that is a vaccine produced using the cells of other organisms belonging to the same species (e.g. Scappaticci F. A., Nolan G. P., "Induction of anti-tumor immunity in mice using a syngeneic endothelial cell vaccine", Anticancer Res., 2003, v. 23, 1165-1672, authors of this publication compare different variants of EC vaccines). The presence of allogenic antigens in vaccines also results in the decrease of the strength and of the specificity of immune response to the EC-specific antigens.

The closest analogue is described in the paper of Okaji Y. et al. ("Vaccination with autologous endothelium inhibits angiogenesis and metastasis of colon cancer through autoimmunity", Cancer Sci., 2004, v. 95, 1, 85-90). The latter method includes the use of endothelial cells. In the above mentioned method autological EC are used i.e. the cells isolated from the organism vaccinated or cells from the genetically identical organisms (e.g. cells from the same line of mice). Such vaccines give a most strong and specific immune response determining the cure effect. But all of vaccines obtained from the whole cells contain a large quantity of ballast material i.e. of cytosol proteins, carbohydrates and lipids. Ballast substances strongly reduce the part of antigens in the vaccine, these antigens being the potential aim for the action of the immune system (intracellular antigens are not available to the effect of the immune system). One should note that an already known method of the preparing of the vaccine does not induce the specific immune response to the EC of tumor vessels namely.

The aim of this invention is the development of the method of preparing EC antigens-based tumor vaccine intended for the overcoming of the immune tolerance of organism to the EC of the tumor vessels. The ground for this invention is a well known difference between the EC of normal tissue vessels, which are in a state of rest under physiological conditions, and the EC of tumors which are activated i.e. are actively proliferating and migrating. It is known that activated EC in comparison with the EC of normal tissue vessels have a higher expression of many specific proteins such as $\alpha_v\beta_3$ (Gladson C. L. et al., Am. J. Pathol., 1996, v. 148, 1423-1434), E-selectin (Volm M. et al., Clin. Cancer Res., 2000, v. 6, 3236-3240), endoglin (Burrows F. et al., Clin. Cancer Res., 1995, v. 1, 1623-1634), endosyalin (Takahashi K. et al., J. Clin. Invest., 1994, v. 93, 2357-64) and VEGF-receptors (Boocock C. et al., J. Natl. Cancer Inst., 1995, v. 87, 506-516). The difference of expression profiles of some proteins is known from the patents US2006210975, US2005142138, US2006127902 and international application WO 2004091383. As to what concerns this invention most important are the differentiae of the EC surface, particularly of the neutrophillins, integrins, receptors etc which allows to obtain antigens specific for the EC of tumor vessels (see international application WO 2004001004).

SUMMARY OF THE INVENTION

The technical result obtained by the use of the invention described in this application consists in the enhancement of the efficiency of oncological disease treatment because of damage done to the tumor vessels by overcoming the immune tolerance of organism to EC of tumor vessels. The meaning is the overcoming of the tolerance namely to the activated EC which permits to cause damage particularly to the tumor vessels.

The above claimed technical result is obtained through the realization of the method of preparing of the tumor vaccine using EC. Accordingly to this invention the live EC undergo the non-deadly for them action of a protease, the splitted antigens are collected, the treatment of the live cells is repeated after intervals necessary for the cells to recover their surface antigens, the surface antigens are accumulated until their dose necessary for the vaccination is obtained, the quality of the prepared vaccine is controlled.

The preferential mode of realization includes the use of activated EC.

The activated EC freshly isolated from the tumor vessels could be possibly used.

If the quantity of isolated from tumor vessels EC is insufficient the method also assumes the multiplication of the EC by their cultivation.

In the preferential variant of realization trypsin is used as a protease.

The activated EC could be isolated from tumor vessels and cultivated under conditions maintaining their active state.

The activated state of EC could be supported by co-cultivation with tumor cells.

The other variant of realization makes possible the maintaining of the activated state of the EC by cultivation in the presence of the tumor tissue fragments.

In the preferential variant of realization the activated EC are obtained from the tumor vessels of the patient himself.

In the other variants activated EC from the tumor vessels of diverse patient could be used.

Also could be used the EC culture activated by the in-vitro co-cultivation with tumor cells.

EC could be activated by the patient's own tumor cells.

Another possible variant includes the activation of EC by the tumor cells of some other patient. EC could be activated by an appropriate tumor cell line.

Other variants of realization presume the use of EC culture activated in-vitro by the addition of activating factors. In that case the EC could be activated by at least one activating factor. In particular EC are activated with the use of Vessel Endothelium Growth Factor (VEGF).

Another variant is the use of EC activated in-vitro by the addition of the conditioned medium from the tumor cell culture.

The enhancement of the immune response is obtained when adjuvants are added to the surface antigens.

BRIEF DESCRIPTION OF THE DRAWINGS

Further the invention is illustrated by the particular examples of realization and by the corresponding figures which represent the next.

DETAILED DESCRIPTION OF THE PREFERRED EMBODIMENTS

Figure 1:
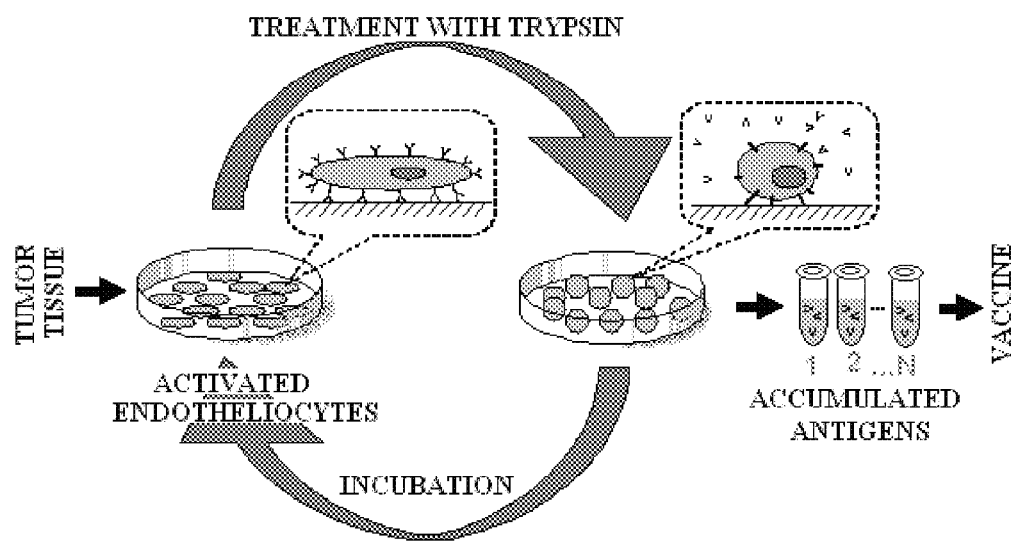
FIG. 1. The schema of the variant of realization of the vaccine preparation.

On the FIG. 1 the variant of realization of the method is explained. Live EC are isolated from the tumor tissue obtained by biopsy or operation. Live EC are used for the initiation of the primary culture of activated EC. At need the cells are cultivated until their necessary quantity is obtained.

Not only tumor vessels EC which are in the activated state from the beginning, but also EC from normal vessels in resting state and EC activated by various means could be used for the realization of the method described in the application.

The next crucial step of invention is the treatment of live cells with a protease at mild (non-deadly for cells) conditions.

In order to obtain the necessary for the vaccination dose of antigens the procedure of treatment of the cells with trypsin is repeated several times with time intervals from some hours to few days necessary for the reparation of surface antigens. Antigens accumulated by this way are treated accordingly to the technology of preparation of the particular vaccine i.e. those antigens could be purified, concentrated, analyzed as for their composition and also modified or mixed with adjuvants for the enhancement of immunogenity.

The preparation of antigens for the vaccination according to the invention has the next advantages:
- all of the advantages of the auto-vaccines i.e. their specificity relatively the particular patient;
- all of the advantages of polyvalent vaccines i.e. the multiplicity of antigens;
- the enrichment of the vaccine by the surface antigens of EC (better use activated EC) that provides the overcoming of the immune tolerance to tumor vessels EC following the immunization;
- the possibility to obtain a necessary for the vaccination dose of antigens by their accumulation but not by the proliferation of EC, which is capital because the primary cell cultures during their proliferation in-vitro slowly change their antigenic structure and become unusable for the vaccination.

The practical use of surface antigens obtained accordingly to this description depends on their identity with the protein fragments present on the surface of the vessels' EC (including tumors) i.e. on the identity of amino acid sequences and their modifications (e.g. glycosylation). The use of the surface antigens of activated EC obtained accordingly to this invention is conditioned by their identity with protein fragments present on the EC surface namely of the tumor vessels.

It is known that tumor growth is impossible without tumor vascularisation. Accumulated and purified EC surface antigens (activated by preference) mixed with the adjuvant which enhances immune response are injected in humans or animals. As a result of cell and humoral immune response which inactivates injected antigens already existing EC or the newly appearing one's in the tumor vessels are cross-destroyed, which determines the healing and prophylactic effects of the immunization. In order to obtain a full immune response reiterated injections of surface antigens are made.

Follows the first example of realization of the method of preparing of the tumor vaccine against human hepatoma H22 inoculated to mice on the basis of the autologous activated EC.

The culture of autologous EC is obtained from the vessels of the liver of BALB/c mice accordingly to Belloni et al. (Microvasc. Res., 1992, vol. 43, 20-45). The activation of EC is performed by adding of the conditioned growth medium from H22 cells into the EC growth medium in the proportion 1:3. To the 5-7$^{th}$ days after the activation the EC are used to obtain surface antigens according to the next protocol.

1. The growth medium is removed from the flask with the culture of activated EC, the monolayer of cells is washed no less then three times with (half the volume of growth medium) sterile physiological solution. This wash-out is performed for the removing of the remainders of the growth medium.

The next and also the crucial step is the treatment of the cells with vital for those cells concentration of protease, as for protease the trypsin is the choice (activity ~3000 U/mg).

2. The 0.0001% solution of the trypsin is added to the monolayer of cells using 1 ml of the solution for every 25 $cm^2$ of flask surface.

3. The flask is incubated at 37° C. Between 5-7 minutes of incubation the trypsin solution containing the splitted surface antigens is removed.

4. A new freshly prepared growth medium containing the serum (usually 10%) is added and the cultivation follows.

5. For the fabrication of the necessary for the vaccination dose the surface antigens are accumulated, the steps 1-4 are repeated at 24 hours intervals, the quality of the vaccine is controlled by checking the suitability of the culture of activated EC for the purpose of obtaining of tumor vessels specific antigens.

The conditions of the treatment of the cells with the protease could vary significantly e.g. from few minutes to some dozens minutes, the trypsin concentration could vary from 0.00001% to 0.5%, the conditions are adopted individually for every primary culture of EC. If the activity of the trypsin differs from that given in the description it's concentration is calculated according to the right proportion of it's activity.

Immediately before the treatment with trypsin the cells should be washed e.g. with physiological solution in order to remove the remainders of the growth medium. Antigens released under the trypsin treatment are fragments of surface proteins, they are collected by any suitable procedure e.g. by pipette's decantation.

During the process of cultivation the antigenic composition of EC as that of any cultivated cells is changing which leads to the discrepancy between antigens of the cell culture and the antigens from the surface of EC of patient's tumor vessels. In order to prevent the fabrication of the non-suitable vaccine the adequacy of EC culture for the antigen accumulation is tested accordingly to the method of assessing of cell cultures described in the Eurasian patent No 009326 "Method for testing a cell culture quality".

It is known that the treatment of the cells with non-deadly (for them) protease concentration leads to the splitting of the surface cell antigens (see for example the Eurasian patent No 009325 "Tumor vaccine, a method for producing a tumor vaccine and a method for carrying out anti-tumor immunotherapy"). So accordingly to this invention the action of trypsin as also of other proteases leads to releasing into the solution of surface antigens of EC. Surface EC antigens (fragments of the surface proteins) released under the action of trypsin are for the most part those suitable for the immunization, and are used for the vaccination of oncological patients.

N.B. that the collection of the trypsin solution containing antigens splitted from the cell surface proteins is better to perform before the moment of detachment of the cells from the surface of the flask, it will help to prevent the appearance of cells in the antigen solution and thus avoid the unnecessary purification step.

The cells do not perish following the vital protease treatment under appropriate concentration which gives the possibility to reiterate the treatment of the primary EC culture with trypsin for the accumulation of the necessary dose of antigens for vaccination.

During the intervals between the trypsin treatment the cells are incubated according to the protocol of cultivation (i.e. at 37° C. in the $CO_2$-incubator, growth medium with the serum and necessary for the active state maintenance additions).

Accumulated surface antigens are treated accordingly to the technology of manufacturing of the vaccine, namely could undergo purification, concentration, composition analysis and also modification or mixing with adjuvants for the enhancement of immunogenity.

In the other variants of realization of the said invention the process of treatment of the cells with the protease could be coupled with the process of the cells subcultivation (cell treatment with protease, cell harvesting and splitting).

Trypsin solution could be prepared using sterile physiological solution, and using also any appropriate salt or buffer solution.

In the other variants of realization of the invention different proteases could be used instead of trypsin e.g. chemotrypsin, protease K etc.

This (intended for application) method of preparation of tumor vaccine could be applied to any variation of EC culture, in particular to the cultures on matrix or on substrate, different combinations of co-cultivation are possible to use as well as freshly isolated EC.

Further the invention is illustrated by the second example of the method of preparation of tumor vaccine using the primary culture of activated EC isolated from the vessels of the human colon cancer.

1. A piece of the tissue of colon tumor obtained during the surgical ablation of the tumor was put into the sterile tube with RPMI 1640 medium containing antibiotics and was transported into the laboratory.
2. Under sterile conditions the tumor tissue is translocated into the Petri dish, sites of necrosis, blood clots and the remnants of fat and connective tissue were removed mechanically.
3. The tumor tissue is cut into small pieces with scissors.
4. The fragments of tumor tissue are incubated in 0.2% solution of collagenase at 37° C. in the volume sufficient to cover the tumor fragments.
5. The collagenase solution is discarded and tumor tissue fragments are gently washed with PBS solution.
6. Three ml of RPMI 1640 medium are added, the fragments of tumor tissue are reduced into small cell aggregates by means of intensive soaking up and blowing out through the pipette ending.
7. Bigger aggregates are left to fall on the bottom, the remaining cells are translocated into a new tube and centrifuged at 170 g at room temperature.
8. The cell pellet is resuspended in RPMI 1640 medium.
9. 1 ml of the cell suspension is centrifuged in the Percoll gradient during 20 minutes at 670 g at room temperature.
10. The cell fraction corresponding to the Percoll gradient density 1.033-1.047 (it corresponds to EC) is collected, 10 ml of RPMI 1640 are added, the mixture is resuspended and the cells collected by the 5-minutes centrifugation at 170 g.
11. EC are resuspended in growth medium (RPMI 1640, heparin, endothelial growth factor, conditioned medium of tumor cells, 10% fetal calf serum) and cultivated in the culture flask.
12. The medium growth is discarded out of the flask, cells are washed three times with physiological solution or PBS solution using half the volume of the cultivation medium. As a result the traces of the serum originating from the growth medium should be removed.

13. 0.0001% solution of the trypsin (the activity ~3000 U/mg) is added to the cells, using 1 ml of the solution for every 25 cm$^2$ of the flask surface.
14. The flask is incubated at 37° C. Between 5 and 7 minutes of incubation the solution containing the released surface antigens is collected. During the removal of the solution from the flask the EC should remain attached to the bottom of the flask. If under the effect of trypsin a part of the cells was detached from the flask surface and float in the liquid then the solution must undergo centrifugation at 400 g during 5 minutes, the cell-free supernatant is used.
15. For the inactivation of the rests of trypsin in the flask with EC it is necessary to add fresh culture medium containing calf serum and continue the incubation at 37° C. and 5% $CO_2$.
16. The solution obtained accordingly to the p. 14 undergoes concentration using vacuum concentrator at 45° C. Previously the solution should be desalted in any appropriate way e.g. by reverse phase chromatography, by the gel-filtration etc.
17. For the accumulation of the necessary quantities of antigens pp. 12-16 are reiterated at time intervals from few hours to few days, during which period the quality of the vaccine under preparation is controlled by means of assessing the EC in relation to their suitability for the obtaining of antigens specific for the tumor vessels of the patient.

In the preferential variant of realization of the invention EC are co-cultivated with tumor cell stemming from the same tumor out of which EC were isolated.

In another variant of realization of the invention EC are co-cultivated with tumor cells stemming from the tumor of other patient or co-cultivated with the particular line of tumor cells.

In another variant of realization of the invention EC are co-cultivated with fragments of the tumor used for the isolation of those EC, or co-cultivated with the tumor fragments of some other patient.

In another variant of realization of the invention the activated EC are stemming from other patient (allogenic EC).

The surface antigens of the cultivated EC obtained according to this invention must be specific for the EC of the donor tumor. But the cultivation distorts the phenotype of the cells because of the impossibility to create in-vitro the same conditions under which the tumor cells are growing in the patient's organism. Thus the suitability of the EC culture for the accumulation of antigens for the vaccination should be controlled in obligatory way and also should be performed according to the method described in the beforementioned Eurasian patent "Method for testing a cell culture quality".

In order to corroborate the anti-tumor activity of the vaccine obtained according to the said invention the model experiment on mice was performed, three groups of BALB/c mice (6 males per group) of the same age and weight were used.

Antigens were prepared according to the first mode of realization of the invention using cultures of authologous activated and non-activated EC. The antigens isolated were desalted by the gel-filtration on Sephadex G-10 and further concentrated on the vacuum concentrator.

The mice were injected subcutaneously with one million hepatoma H22 cells. On the 7$^{th}$ day after injection mice were vaccinated by subcutaneous injection of 150 µg of antigens previously mixed with complete Freund's adjuvant at the ratio 1:1 (v/v). The subsequent immunizations were performed during 4 weeks using incomplete Freund's adjuvant once per week Animals of the first experimental group were inoculated with the vaccine made according to first mode of realization of the invention i.e. with the use of authologous activated EC. Animals of the second group were inoculated with the vaccine made according to the first mode of realization of invention using authologous but non-activated EC. The control group was injected with PBS mixed with Freund's adjuvant using the same schema.

Figure 2:
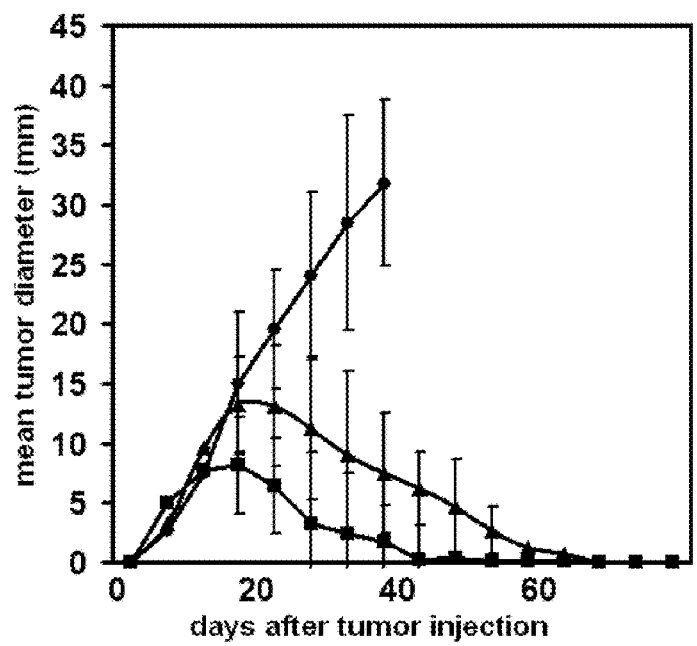
FIG. 2. Curves of the growth of hepatoma H22 on mice BALB/c in the first and second experimental groups and in the control group (the mean dimensions of tumor are shown±standard deviation).

During three months after the inoculation of the tumors their growth was observed in control and experimental groups. Measurement results (see FIG. 2) demonstrate the reduction and disappearance of tumors in animals of experimental groups which proves the marked anti-tumor effect of the vaccine containing surface EC antigens, the more pronounced effect is observed with the vaccine elaborated on the base of surface antigens of activated EC.

For the corroboration of the anti-vessel mechanism of action of the vaccine Angiogenic Indices (quantity of vessels per 1000 tumor cells) were measured in tumors of the control and experimental groups, using histological slices and immunoenzyme method of dying the walls of tumor vessels.

Freshly isolated fragments of tumor tissue taken on the 30$^{th}$ day after the tumor inoculation were fixed in 10% formaldehyde solution in PBS (pH 7.0-7.2) and embedded into paraffin. For the immunohistochemical investigation of 4 µm thick sections were prepared. To reveal vessels the sections were stained with murine antibodies to human CD31 using the standard avidin-biotin-peroxidase protocol. Paraffin was removed with ethanol. The endogenic peroxidase activity was blocked with 3% hydrogenium peroxide. The non-specific binding of antibodies was prevented with 3% BSA solution in PBS. The sections were consequently incubated with primary antibodies to CD31, biotinilated antibodies to murine IgG and streptavidin-biotin-peroxidase complex. Sections were stained with freshly prepared solution of diaminobenzidine and poststained with hematoxilin. After each step sections were washed by PBS. As negative control sections were used, stained accordingly to the descried above method where primary antibodies were substitute by murine IgG.

Figure 3:
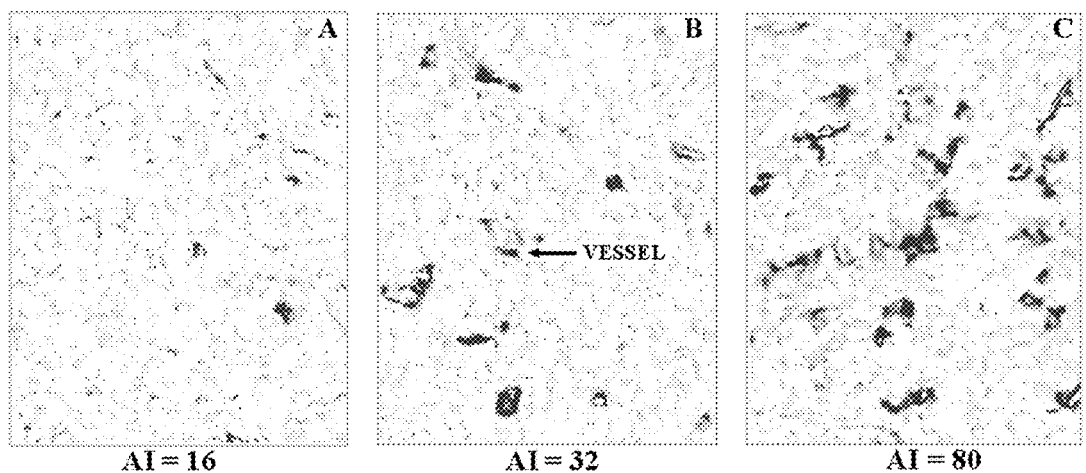
FIG. 3. Histological sections of the tumor tissues of the first (A), second (B) and control (C) group of mice are shown and their corresponding Angiogenic Indices (AI); the wall of the tumor vessels are colored dark (it corresponds to the brown color on the color photo).

FIG. 3 demonstrates the histological sections of tumors of the first (A) and second (B) experimental groups and of the control group (C), to these groups correspond the Angiogenic Indices (AI) equal to 16, 32 and 80. This fact confirms the inhibition of the vascularisation as the result of vaccination by the surface antigens of EC, mark that the more strong inhibition corresponds to the vaccine based on activated EC.

It is to stress that the results of the model experiment are not restricted to the animal use because the mechanisms of immune response are identical both in human and animals.

The method of administration of the antigens and their dose calculated for 1 kg weight conserve their meaning in cases of immunization of human, but the immunization schema (dose, number of repeated injections and also the used adjuvants) could be individualized for each particular patient, taking into account the seriousness of diseases development, the phase of the oncological disease, the degree of vascularisation of the tumor, the aptitude of the organism for the marked immune response to antigens paralleled by chemotherapy.

Below the example is given how to obtain an tumor vaccine based on surface EC antigens, the vaccine was prepared according to the second variant of realization of the invention for the anti-tumor vaccination of men.

The vaccine consists of 1 mg of antigen mixture (prepared according to the second variant of realization of the invention) dissolved in 0.5 ml PBS and mixed with 1 ml adjuvant Montanide ISA-51 (it's the adjuvant of the firma "Syntex" developed on the base of water-oil emulsion and containing squalene, Plunoric L121, Tween 80).

One dose of the vaccine is injected to the patient subcutaneously every week during three weeks and once per month during five months.

The efficiency of vaccination is checked by the intensity of immunity to injected surface antigens. On the 2 d-3 d day after injection the reaction of hypersensitivity against injected antigens is assessed taking into account the dimension of the red spot at the place of injection. As a base index the dimension on the place of the first injection is accepted. The evident enhancement of hypersensitivity reaction after repeated vaccination indicates the developing immune response.

The intra-venous or intra-muscular injection of the vaccine is also possible, the injection of vaccine without the adjuvant is possible as well.

The development of the immune response after the use of vaccine prepared accordingly to the application method is due to the presence of surface EC antigens in the vaccine. The plurality of antigens i.e. of the fragments of surface proteins present in the vaccine makes possible the immune response against all of cells which have on their surface proteins with the same amino acid sequences.

The preparation of tumor vaccines accordingly to this method could be effected using not only the activated EC of the patient himself but also using the EC of another patient.

In both cases the effect of cure is achieved because of the presence on the surface of the EC of tumor vessels from different patients of the antigens with identical amino acid sequences. And yet when auto-vaccines prepared according to the said method are used the effect is more pronounced because in this case the vaccine contains antigens which are individual for the EC of the tumor vessels of the particular patient.

The effect of the cure is also attained in the case of the use of EC from normal tissues both in resting state or activated by various methods. This effect is explained by the presence of surface antigens common to all EC and also by partly common character of changes in the antigen composition of EC following their activation by various methods.

One should note that the use of vaccines obtained according to this method, which is proposed as application, permits to enhance the effectiveness of treatment many times in comparison with the use of monovalent vaccines.

The use of the vaccine prepared according to the method under application give the possibility to overcome the immune tolerance of organism to EC of tumor vessels because the vaccine is enriched with antigens specific for the tumor vessels EC.

This possibility is created because of the protease treatment of the cells with vital (non-deadly) for these cells protease concentration. The use of the vital protease concentration permits to cleave off only the surface antigens of EC and to avoid the death of the cells followed by the destruction of their plasmatic membranes which leads to the contamination of the vaccine by cytoplasm content particularly with a mass of intra-cell proteins which are useless for the vaccination. This process is known to diminish the part of specific tumor vessel antigens in already known vaccines, it leads to the inducing of the untargeted immune response and as consequence the diminishment of it's specificity against namely surface antigens.

So the use of the vaccine enriched with surface antigens, the vaccine prepared accordingly to this invention, permits to enhance the efficiency of anti-tumor therapy.

Besides the enhancement of efficiency of the immunotherapy is obtained through the use of surface antigens prepared by the accumulation of antigens obtained from the identical EC. Such method of the preparing of the tumor vaccine permits to obtain by every use of the protease the antigens of practically unchanged composition and accumulate the quantity of antigens necessary for the vaccination. The incorporation into the vaccine of only specific to the particular tumor vessels antigens is secured by the possibility of control of the quality of vaccine.

So the invention gives the possibility to obtain surface antigens of EC and to perform on it's base the immunotherapy of oncological diseases, namely the vaccination.

The invention claimed is:

1. A method of preparing a tumor cell vaccine comprising treating live, activated endothelial cells with trypsin having activity of at least 3000 U/mg and concentration from 0.00001% to 0.5% under conditions non-deadly for endothelial cells, and collecting released cell surface antigens, wherein the endothelial cells are activated in vitro by adding a conditioned growth medium from a tumor cell culture.

2. The method of claim 1 wherein the endothelial cells are freshly isolated from tumor tissue vessels.

3. The method of claim 1 wherein the live endothelial cells are cultivated for multiplication prior to treatment with trypsin and collection of the released cell surface antigens.

4. The method of according to anyone of claim 1 or 3 wherein the activated endothelial cells are isolated from tumor vessels and are cultivated under conditions maintaining their activated state.

5. The method according to claim 4 wherein the activated state of endothelial cells during cultivation is further supported by co-cultivation with tumor cells.

6. The method according to claim 4 wherein the activated state of endothelial cells during cultivation is further supported by co-cultivation with fragments of tumor tissue.

7. The method according to claim 5 wherein the tumor cells are a tumor cell line.

8. The method according to claim 4 wherein the endothelial cells are further activated using vessel endothelium growth factor (VEGF).

9. The method of claim 1 wherein an adjuvant is added to the collected cell surface antigens.

10. A method of preparing a tumor cell vaccine comprising treating live, activated endothelial cells with trypsin having a concentration from 0.00001% to 0.5% under conditions non-deadly for endothelial cells, and collecting released cell surface antigens, wherein the endothelial cells are activated in vitro by adding a conditioned growth medium from a tumor cell culture.

11. The method of claim 10 wherein an adjuvant is added to the collected cell surface antigens.

12. A method of preparing a tumor vaccine comprising treating live, activated endothelial cells with a protease at conditions non-deadly for endothelial cells, and collecting the released cell surface antigens, wherein the endothelial cells are activated in vitro by adding a conditioned growth medium from a tumor cell culture.

13. The method of claim 12 wherein the collection of released cell surface antigens occurs before detachment of the endothelial cells from the culture surface.

14. The method of claim 12 wherein an adjuvant is added to the collected cell surface antigens.

15. A method of preparing a tumor vaccine comprising treating live, activated endothelial cells with a protease at conditions non-deadly for endothelial cells, and collecting the released cell surface antigens, wherein the activated endothelial cells are isolated from tumor vessels and maintained in an activated state during cultivation prior to the treatment with the protease by the addition of activating substances into the growth medium, wherein the activating substances are at least one of conditioned growth medium from a tumor cell culture, and vessel endothelium growth factor (VEGF).

16. The method of claim 15 wherein the activated state of endothelial cells during cultivation is further supported by co-cultivation with tumor cells.

17. The method of claim 15 wherein the activated state of endothelial cells during cultivation is further supported by co-cultivation with fragments of tumor tissue.

18. The method of claim 15 wherein an adjuvants is added to the collected cell surface antigens.

* * * * *